US00PP08505P

United States Patent [19]

Marciel et al.

[11] Patent Number: Plant 8,505

[45] Date of Patent: Dec. 21, 1993

[54] HYBRID TEA ROSE PLANT NAMED DEVDORADO

[75] Inventors: Stanley G. Marciel; Jeanne A. Marciel, both of Aptos, Calif.

[73] Assignee: DeVor Nurseries, Inc., Watsonville, Calif.

[21] Appl. No.: 974,116

[22] Filed: Nov. 10, 1992

[51] Int. Cl.[5] ..... A01H 5/00

[52] U.S. Cl. ..... Plt./15

[58] Field of Search ..... Plt./11, 15

[56] References Cited

U.S. PATENT DOCUMENTS

P.P. 5,622 1/1986 Meilland ..... Plt. 11

*Primary Examiner*—Howard J. Locker

*Attorney, Agent, or Firm*—Christie, Parker & Hale

[57] ABSTRACT

A new hybrid tea rose plant producing yellow flowers.

1 Drawing Sheet

SUMMARY OF THE INVENTION

The present invention relates to a new and distinct variety of rose plant of the hybrid tea rose class which was originated by my crossing as seed and pollen parents unnamed and unpatented seedlings of my creation. The varietal denomination of this new rose is 'Devdorado'.

Among the novel characteristics possessed by this new variety which distinguish it from its parents and all other varieties of which I am aware are its large, attractive soft yellow flowers with red veins and edging, borne with long stems on a plant particularly suitable for cut-flower production in greenhouses.

Asexual reproduction by budding of the new variety as performed in Watsonville, Calif. shows that the foregoing and other distinguishing characteristics come true to form and are established and transmitted through succeeding propagations.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed seedling (80227-20).

*Pollen parent.*—Unnamed seedling (82249-1).

Class: Hybrid tea.

The following is a detailed description of specimens of my new variety, grown under glass in Watsonville, Calif. in the month of September and with color terminology in accordance with The Royal Horticultural Society Colour Chart (RHSCC). The terminology used in color descriptions herein refers to plate numbers in the aforementioned color chart. Phenotypic expression may vary depending on light and cultural conditions.

FLOWER

Blooming habit: Continuous.

A. Bud:

(1) *Size.*—Large.

(2) *Form.*—Pointed.

(3) *Color.*—As sepals divide, bud color is near 20A.

(4) *Sepals.*—Extend about 2.5 cm above bud; simple to foliaceous. Color: Near 144A.

(5) *Peduncle.*—Length: 7 to 9 cm. Aspect: Slightly curved. Strength: Erect, sturdy. Color: Near 183B.

(6) *Bracts.*—Usually 1 to 2 present, near 187C, broadly elliptical with acute, tip, located about 6 cm below calyx.

B. Bloom:

(1) *Size.*—Average size when fully expanded — about 13 to 14 cm.

(2) *Borne.*—Singly, one to a stem.

(3) *Form.*—High-centered, becoming flat on opening.

(4) *Petalage.*—Number of petals under normal conditions — about 26 to 30; usually few petaloids.

(5) *Color.*—When ⅔ to ½ open, the top surface of the outer petals is near 10C at the top, near 11A at the center and near 14B at the base. The undersurface of the outer petals is near 12D at the top, near 11C at the center and near 8A at the base. The top surface of the inner petals is near 12C at the top, near 13B at the center and near 12A at the base. The undersurface of the inner petals is near 11B at the top, near 11A at the center and near 9B at the base. The base of the petals at the point of attachment is near 9A, and the general tonality from a distance is a deep yellow center with pale yellow outer petals. When fully open, the top surface of the outer petals is reddish along the outer edge of the petal, near 11D at the top, near 4C at the center and near 9A at the base. The undersurface of the outer petals is near 158A at the top, near 9D at the center and near 6B at the base. The top surface of the inner petals is near 20C at the top, near 11C at the center and near 8B at the base. The undersurface of the inner petals is near 8D at the top, near 11B at the center and near 6D at the base. The base of the petals at the point of attachment is near 8B, and the general tonality from a distance is a medium warm yellow center with petals gradually lightening as they go to the outer edge. As the bloom ages, the color changes from a warm golden color to a pale yellow with pink tinge along the outer edge of the petals.

C. Petals.:

(1) *Texture.*—Medium.

(2) *Appearance.*—Inside smooth, outside velvety.
(3) *Form.*—Slightly lobed.
(4) *Arrangement.*—Regularly arranged, imbricated.
(5) *Fragrance.*—Moderate, sweet.
(6) *Lasting quality.*—7 to 8 days as cut flower; petals persist.

REPRODUCTIVE ORGANS

A. Stamens:
(1) *Arrangement.*—Introrse, near 20A.
(2) *Anthers.*—Color — near 23B.
(3) *Filaments (threads).*—Color — near 14B.
(4) *Pollen.*—Color — near 22B.

B. Pistils:
(1) *Styles.*—Bunched, medium length.
(2) *Stigmas.*—Color — near 182A around edges, near 22B inside.

C. Characteristics of hips:
(1) *Shape.*—Globular; seeds do not protrude.
(2) *Size.*—about 3.5 cm to 5.6 cm in length.
(3) *Color at maturity.*—Near 31A.

PLANT

A. Form: Upright, bushy.
B. Growth: Vigorous, uniform branching; height attained about 185 cm in first season.
C. Foliage: Compound 3, 5 and 7 leaflets.
(1) *Size.*—Medium.
(2) *Quantity.*—Abundant.
(3) *Color.*—Upper side — near 147A. Underside — near 147B.
(4) *Shape.*—Oval.
(5) *Texture.*—Leathery.
(6) *Edge.*—Serrate.
(7) *Serration.*—Denticulate.
(8) *Leaf stem.*—Color — medium green.
(9) *Stipules.*—Hairy, adnate, medium length.
(10) *Rachis.*—Occasional small prickles.
(11) *Petioles.*—Top — near 146 D tinged with near 183D. Underside — near 183D with 147D and near 183B at base.
(12) *Resistance to disease.*—Under greenhouse conditions, no rust and block spot; good resistance to mildew.

D. Wood:
(1) *New wood.*—Color — near 166A. Bark — smooth.
(2) *Old wood.*—Color — near 147B. Bark — smooth.

E. Flower stem from last cut.—About 82 to 92 cm.
F. Thorns:
*Quantity (main stalk).*—Average.
*On laterals from stalk.*—Few.
*Form.*—Wing-shaped, curved slightly downward.
*Length.*—Medium.
*Color.*—Near 176A with some 144A at base.
*Position.*—Irregular.
*Prickles.*—Few to none present.

G. Winter hardiness: Greenhouse variety, wintered well in Califronia.

I claim:

1. A new and distinct variety of rose plant of the hybrid tea rose class, substantially as shown and described.

* * * * *

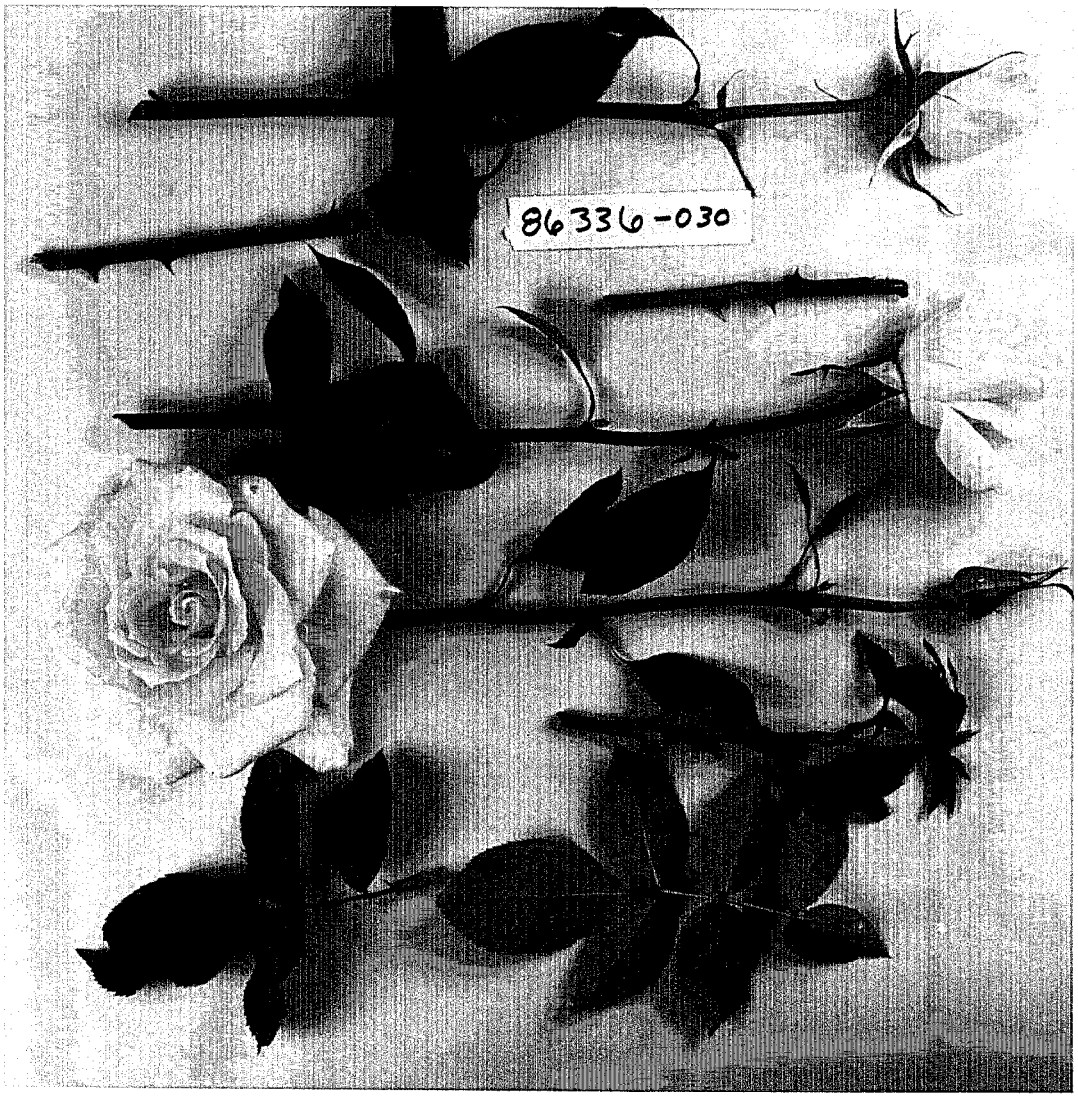
86336-030

UNITED STATES PATENT AND TRADEMARK OFFICE

CERTIFICATE OF CORRECTION

PATENT NO. : Plant 8,505

DATED : December 21, 1993

INVENTOR(S) : Stanley G. Marciel; Jeanne A. Marciel

It is certified that error appears in the above-indentified patent and that said Letters Patent is hereby corrected as shown below:

Column 2, line 7, change "acute, tip," to
-- acute tip, --.

Column 2, line 17, change "2/3 to 1/2 open" to
-- 1/3 to 1/2 open --.

Signed and Sealed this

Twenty-fifth Day of October, 1994

*Attest:*

*Attesting Officer*

Bruce Lehman

BRUCE LEHMAN

*Commissioner of Patents and Trademarks*